US012419551B2

(12) United States Patent
Chatterjee et al.

(10) Patent No.: US 12,419,551 B2
(45) Date of Patent: Sep. 23, 2025

(54) MEDIATION OF IN VIVO ANALYTE SIGNAL DEGRADATION

(71) Applicant: Senseonics, Incorporated, Germantown, MD (US)

(72) Inventors: Joon Chatterjee, Germantown, MD (US); Sanat Mohanty, Germantown, MD (US); Philip Huffstetler, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 1417 days.

(21) Appl. No.: 16/869,161

(22) Filed: May 7, 2020

(65) Prior Publication Data
US 2020/0352492 A1    Nov. 12, 2020

Related U.S. Application Data

(60) Provisional application No. 62/845,020, filed on May 8, 2019.

(51) Int. Cl.
| | |
|---|---|
| *A61B 5/1473* | (2006.01) |
| *A61B 5/1468* | (2006.01) |
| *A61L 31/04* | (2006.01) |
| *A61L 31/10* | (2006.01) |
| *A61L 31/14* | (2006.01) |
| *C07C 323/52* | (2006.01) |
| *C07C 323/56* | (2006.01) |
| *C08K 5/37* | (2006.01) |

(52) U.S. Cl.
CPC ........ *A61B 5/14735* (2013.01); *A61L 31/041* (2013.01); *A61L 31/10* (2013.01); *A61L 31/145* (2013.01); *C07C 323/52* (2013.01); *C07C 323/56* (2013.01); *C08K 5/37* (2013.01); *A61B 2562/12* (2013.01); *A61B 2562/18* (2013.01)

(58) Field of Classification Search
CPC ............ A61B 5/14735; A61B 2562/12; A61B 2562/18; A61B 5/14532; A61B 5/1459; A61B 5/686; A61L 31/041; A61L 31/10; A61L 31/145; C07C 323/52; C07C 323/56; C08K 5/37

See application file for complete search history.

(56) References Cited

U.S. PATENT DOCUMENTS

| | | | |
|---|---|---|---|
| 5,512,246 | A | 4/1996 | Russell et al. |
| 5,517,313 | A | 5/1996 | Colvin, Jr. |
| 8,277,713 | B2 | 10/2012 | Petisce et al. |
| 8,615,282 | B2 | 12/2013 | Brister et al. |

(Continued)

FOREIGN PATENT DOCUMENTS

| | | |
|---|---|---|
| JP | 2005-315871 A | 11/2005 |
| JP | 2006-111719 A | 4/2006 |

*Primary Examiner* — Navin Natnithithadha
(74) *Attorney, Agent, or Firm* — Rothwell, Figg, Ernst & Manbeck, P.C.

(57) ABSTRACT

A sensor (e.g., an optical sensor) that may be implanted within a living animal (e.g., a human) and may be used to measure an analyte (e.g., glucose or oxygen) in a medium (e.g., interstitial fluid, blood, or intraperitoneal fluid) within the animal. The sensor may include a sensor housing, an analyte indicator covering at least a portion of the sensor housing, and one or more compounds having dithio-, thio- or mercapto-containing moieties that reduce degradation of the analyte indicator.

28 Claims, 4 Drawing Sheets

(56) References Cited

U.S. PATENT DOCUMENTS

| | | | |
|---|---|---|---|
| 8,652,043 B2 | 2/2014 | Drucker et al. | |
| 9,414,775 B2 | 8/2016 | Colvin, Jr. et al. | |
| 9,427,181 B2 | 8/2016 | Emken et al. | |
| 9,681,824 B2 | 6/2017 | Colvin, Jr. et al. | |
| 9,693,714 B2 | 7/2017 | DeHennis et al. | |
| 9,931,068 B2 | 4/2018 | Huffstetler et al. | |
| 10,172,791 B2 * | 1/2019 | Ma | A61K 9/0024 |
| 2007/0235331 A1 | 10/2007 | Simpson et al. | |
| 2007/0270675 A1 | 11/2007 | Kane et al. | |
| 2008/0234561 A1 | 9/2008 | Roesicke et al. | |
| 2011/0236989 A1 | 9/2011 | Suri et al. | |
| 2013/0241745 A1 | 9/2013 | Colvin, Jr. et al. | |
| 2015/0057509 A1 | 2/2015 | Huffstetler et al. | |
| 2016/0244554 A1 * | 8/2016 | Cheng | A61L 27/18 |
| 2017/0360994 A1 * | 12/2017 | Havenstrite | A61L 29/085 |
| 2018/0220940 A1 | 8/2018 | Huffstetler et al. | |

* cited by examiner

Glucose modulation remaining (normalized to Day 0)

| Days (in vivo, Guinea Pig) | % Glucose Modulation remaining | | | | |
|---|---|---|---|---|---|
| | 0 | 30 | 48 | 65 | 90 |
| CONTROL | 100% | 48% | 34% | 28% | 22% |
| Dithio-containing compound, DTDP | 100% | 80% | 80% | 63% | 47% |

FIG. 4

MEDIATION OF IN VIVO ANALYTE SIGNAL DEGRADATION

CROSS-REFERENCE TO RELATED APPLICATION

The present application claims the benefit of priority to U.S. Provisional Application Ser. No. 62/845,020, filed on May 8, 2019, which is incorporated herein by reference in its entirety.

BACKGROUND

Field of Invention

The present invention relates generally to continuous reduction of in vivo degradation of analyte sensor moieties when measuring an analyte in a medium of a living animal using a system including a sensor implanted (partially or fully) or inserted into the living animal. Specifically, the present invention relates to a sensor that utilizes one or more additives, which may be incorporated within an analyte indicator and/or a material covering at least a portion of the analyte indicator.

Discussion of the Background

A sensor may be implanted (partially or fully) within a living animal (e.g., a human) and used to measure an analyte (e.g., glucose, oxygen, cardiac markers, low-density lipoprotein (LDL), high-density lipoprotein (HDL), or triglycerides) in a medium (e.g., interstitial fluid (ISF), blood, or intraperitoneal fluid) within the living animal. The sensor may include a light source (e.g., a light-emitting diode (LED) or other light emitting element), indicator molecules, and a photodetector (e.g., a photodiode, phototransistor, photoresistor or other photosensitive element). Examples of implantable sensors employing indicator molecules to measure an analyte are described in U.S. Pat. Nos. 5,517,313 and 5,512,246, which are incorporated herein by reference in their entirety.

A sensor may include an analyte indicator, which may be in the form of indicator molecules embedded in a graft (i.e., layer or matrix). For example, in an implantable fluorescence-based glucose sensor, fluorescent indicator molecules may reversibly bind glucose and, when irradiated with excitation light (e.g., light having a wavelength of approximately 378 nm), emit an amount of light (e.g., light in the range of 400 to 500 nm) that depends on whether glucose is bound to the indicator molecule.

If a sensor is implanted in the body of a living animal, the animal's immune system may begin to attack the sensor. For instance, if a sensor is implanted in a human, white blood cells may attack the sensor as a foreign body, and, in the initial immune system onslaught, neutrophils may be the primary white blood cells attacking the sensor. The defense mechanism of neutrophils includes the release of highly caustic substances known as reactive oxygen species. The reactive oxygen species include, for example, hydrogen peroxide.

Hydrogen peroxide and other reactive species such as reactive oxygen and nitrogen species may degrade the indicator molecules of an analyte indicator. For instance, in indicator molecules having a boronate group, hydrogen peroxide may degrade the indicator molecules by oxidizing the boronate group, thus disabling the ability of the indicator molecule to bind glucose.

There is presently a need in the art for improvements in reducing analyte indicator degradation. There is also a need in the art for continuous analyte sensors having increased longevity.

SUMMARY

The present invention overcomes the disadvantages of prior systems by providing, among other advantages, reduced analyte indicator degradation.

One aspect of the present invention provides a sensor that may be for implantation or insertion within a living animal and measurement of an analyte in a medium within the living animal. The sensor may include a sensor housing, an analyte indicator covering at least a portion of the sensor housing, and one or more additives that reduce deterioration of the analyte indicator.

In some embodiments, the sensor may include at least one additive-containing polymer graft, and the one or more additives may be co-polymerized with or dispersed within the additive-containing polymer graft. In some embodiments, the additive-containing polymer graft may cover at least a portion of the sensor housing. In some embodiments, the additive-containing polymer graft may be within the sensor housing.

In some embodiments, the one or more additives may be incorporated with the analyte indicator, e.g., as a co-monomer. In some embodiments, the sensor may include a material, e.g., a membrane, covering at least a portion of the analyte indicator, and the one or more additives are incorporated within the material.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

FIG. 4 shows percentages of glucose modulation remaining over different durations of implant times inside guinea pigs for samples that included dithio-containing compounds as additives compared to controls, which did not contain dithio-containing compounds.

DETAILED DESCRIPTION OF PREFERRED EMBODIMENTS

Figure 1:
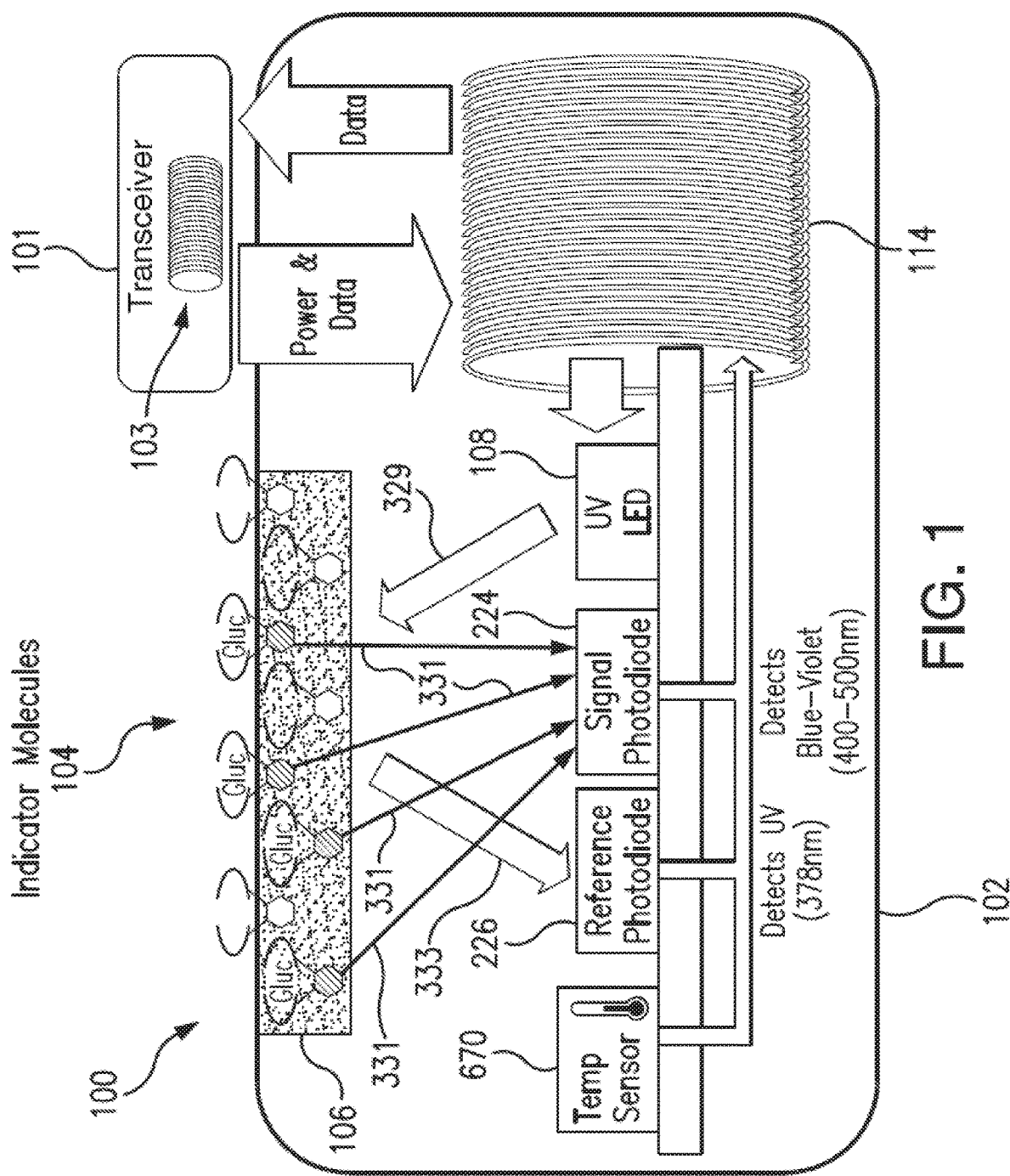
FIG. 1 is a schematic view illustrating a sensor system embodying aspects of the present invention.

FIG. 1 is a schematic view of a sensor system embodying aspects of the present invention. In some non-limiting embodiment, as shown in FIG. 1, the system may include a sensor 100 and an external transceiver 101. In some embodiments, the sensor 100 may be an implantable sensor configured to be fully or partially implanted in a living animal (e.g., a living human). The sensor 100 may be implanted, for example, in a living animal's arm, wrist, leg, abdomen, peritoneum, or other region of the living animal suitable for sensor implantation. For example, in some non-limiting embodiments, the sensor 100 may be implanted beneath the skin (i.e., in the subcutaneous or peritoneal tissues). However, this is not required, and, in some alternative embodiments, the sensor 100 may be a transcutaneous sensor.

In some embodiments, a transceiver 101 may be an electronic device that communicates with the sensor 100 to power the sensor 100, provide commands and/or data to the sensor 100, and/or receive data from the sensor 100. In some embodiments, the received data may include one or more sensor measurements. In some embodiments, the sensor measurements may include, for example and without limitation, one or more light measurements from one or more photodetectors of the sensor 100 and/or one or more temperature measurements from one or more temperature sensors of the sensor 100. In some embodiments, the transceiver 101 may calculate analyte (e.g., glucose) concentrations from the measurement information received from the sensor 100.

In some non-limiting embodiments, the transceiver 101 may be a handheld device or an on-body/wearable device. For example, in some embodiments where the transceiver 101 is an on-body/wearable device, the transceiver 101 may be held in place by a band (e.g., an armband or wristband) and/or adhesive, and the transceiver 101 may convey (e.g., periodically, such as every two minutes, and/or upon user initiation) measurement commands (i.e., requests for measurement information) to the sensor 100. In some embodiments where the transceiver 101 is a handheld device, positioning (i.e., hovering or swiping/waving/passing) the transceiver 101 within range over the sensor implant site (i.e., within proximity of the sensor 100) may cause the transceiver 101 to automatically convey a measurement command to the sensor 100 and receive a data from the sensor 100.

In some embodiments, as shown in FIG. 1, the transceiver 101 may include an inductive element 103, such as, for example, a coil. In some embodiments, the transceiver 101 may generate an electromagnetic wave or electrodynamic field (e.g., by using a coil) to induce a current in an inductive element 114 of the sensor 100. In some non-limiting embodiments, the sensor 100 may use the current induced in the inductive element 114 to power the sensor 100. However, this is not required, and, in some alternative embodiments, the sensor 100 may be powered by an internal power source (e.g., a battery).

In some embodiments, the transceiver 101 may convey data (e.g., commands) to the sensor 100. For example, in some non-limiting embodiments, the transceiver 101 may convey data by modulating the electromagnetic wave generated by the inductive element 103 (e.g., by modulating the current flowing through the inductive element 103 of the transceiver 101). In some embodiments, the sensor 100 may detect/extract the modulation in the electromagnetic wave generated by the transceiver 101. Moreover, the transceiver 101 may receive data (e.g., one or more sensor measurements) from the sensor 100. For example, in some non-limiting embodiments, the transceiver 101 may receive data by detecting modulations in the electromagnetic wave generated by the sensor 100, e.g., by detecting modulations in the current flowing through the inductive element 103 of the transceiver 101.

In some embodiments, as shown in FIG. 1, the sensor 100 may include a sensor housing 102 (i.e., body, shell, capsule, or encasement), which may be rigid and biocompatible. In exemplary embodiments, sensor housing 102 may be formed from a suitable, optically transmissive polymer material, such as, for example, acrylic polymers (e.g., polymethylmethacrylate (PMMA)).

In some embodiments, as shown in FIG. 1, the sensor 100 may include an analyte indicator 106. In some non-limiting embodiments, the analyte indicator 106 may be a polymer graft coated, diffused, adhered, or embedded on at least a portion of the exterior surface of the sensor housing 102. The analyte indicator 106 (e.g., polymer graft) may cover the entire surface of sensor housing 102 or only one or more portions of the surface of housing 102. As an alternative to coating the analyte indicator 106 on the outer surface of sensor housing 102, the analyte indicator 106 may be disposed on the outer surface of the sensor housing 102 in other ways, such as by deposition or adhesion. In some embodiments, the analyte indicator 106 may be a fluorescent glucose indicating polymer. In one non-limiting embodiment, the polymer is biocompatible and stable, grafted onto the surface of sensor housing 102, designed to allow for the direct measurement of glucose in interstitial fluid (ISF), blood, or intraperitoneal fluid after implantation of the sensor 100. In some embodiments, the analyte indicator 106 may be a hydrogel.

In some embodiments, the analyte indicator 106 (e.g., polymer graft) of the sensor 100 may include indicator molecules 104. The indicator molecules 104 may be distributed throughout the entire analyte indicator 106 or only throughout one or more portions of the analyte indicator 106. The indicator molecules 104 may be fluorescent indicator molecules (e.g., TFM having the chemical name 9-[N-[6-(4,4,5,5,-tetramethyl-1,3,2-dioxaborolano)-3-(trifluoromethyl)benzyl]-N-[3-(methacrylamido)propylamino] methyl]-10-[N-[6-(4,4,5,5,-tetramethyl-1,3,2-dioxaborolano)-3-(trifluoromethyl)benzyl]-N-[2-(carboxyethyl) amino]methyl]anthracene sodium salt) or light absorbing, non-fluorescent indicator molecules. In some embodiments, the indicator molecules 104 may reversibly bind an analyte (e.g., glucose, oxygen, cardiac markers, low-density lipoprotein (LDL), high-density lipoprotein (HDL), or triglycerides). When an indicator molecule 104 has bound an analyte, the indicator molecule may become fluorescent, in which case the indicator molecule 104 is capable of absorbing (or being excited by) excitation light 329 and emitting light 331. In one non-limiting embodiment, the excitation light 329 may have a wavelength of approximately 378 nm, and the emission light 331 may have a wavelength in the range of 400 to 500 nm. When no analyte is bound, the indicator molecule 104 may be only weakly fluorescent.

In some embodiments, the sensor 100 may include a light source 108, which may be, for example, a light emitting diode (LED) or other light source that emits radiation, including radiation over a range of wavelengths that interact with the indicator molecules 104. In other words, the light source 108 may emit the excitation light 329 that is absorbed by the indicator molecules in the matrix layer/polymer 104. As noted above, in one non-limiting embodiment, the light source 108 may emit excitation light 329 at a wavelength of approximately 378 nm.

In some embodiments, the sensor 100 may also include one or more photodetectors (e.g., photodiodes, phototransistors, photoresistors or other photosensitive elements). For example, in the embodiment illustrated in FIG. 1, sensor 100 has a first photodetector 224 and a second photodetector 226. However, this is not required, and, in some alternative embodiments, the sensor 100 may only include the first photodetector 224. In the case of a fluorescence-based sensor, the one or more photodetectors may be sensitive to fluorescent light emitted by the indicator molecules 104 such that a signal is generated by a photodetector (e.g., photodetector 224) in response thereto that is indicative of the level of fluorescence of the indicator molecules and, thus, the amount of analyte of interest (e.g., glucose).

Some part of the excitation light 329 emitted by the light source 108 may be reflected from the analyte indicator 106 back into the sensor 100 as reflection light 333, and some part of the absorbed excitation light may be emitted as emitted (fluoresced) light 331. In one non-limiting embodiment, the emitted light 331 may have a different wavelength than the wavelength of the excitation light 329. The reflected light 333 and emitted (fluoresced) light 331 may be absorbed by the one or more photodetectors (e.g., first and second photodetectors 224 and 226) within the body of the sensor 100.

Each of the one or more photodetectors may be covered by a filter 112 (see FIG. 3) that allows only a certain subset of wavelengths of light to pass through. In some embodiments, the one or more filters 112 may be thin glass filters. In some embodiments, the one or more filters 112 may be thin film (e.g., dichroic) filters deposited on the glass and may pass only a narrow band of wavelengths and otherwise reflect most of the received light. In some embodiments, the filters may be thin film (dichroic) filters deposited directly onto the photo detectors and may pass only a narrow band of wavelengths and otherwise reflect most of the light received thereby. The filters 112 may be identical (e.g., both filters 112 may allow signals to pass) or different (e.g., one filter 112 may be a reference filter and another filter 112 may be a signal filter).

In one non-limiting embodiment, the second (reference) photodetector 226 may be covered by a reference photodiode filter that passes light at the same wavelength as is emitted from the light source 108 (e.g., 378 nm). The first (signal) photodetector 224 may detect the amount of fluoresced light 331 that is emitted from the molecules 104 in the analyte indicator 106. In one non-limiting embodiment, the peak emission of the indicator molecules 104 may occur around 435 nm, and the first photodetector 224 may be covered by a signal filter that passes light in the range of about 400 nm to 500 nm. In some embodiments, higher glucose levels/concentrations correspond to a greater amount of fluorescence of the molecules 104 in the analyte indicator 106, and, therefore, a greater number of photons striking the first photodetector 224.

In some embodiments, as shown in FIG. 1, the sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components, may be fabricated in the semiconductor substrate 116 with the remainder of the circuitry is secured to the semiconductor substrate 116, which may provide communication paths between the various secured components.

In some embodiments, the one or more of the sensor housing 102, analyte indicator 106, indicator molecules 104, light source 108, photodetectors 224, 226, temperature transducer 670, substrate 116, and inductive element 114 of sensor 100 may include some or all of the features described in one or more of U.S. application Ser. No. 13/761,839, filed on Feb. 7, 2013, U.S. application Ser. No. 13/937,871, filed on Jul. 9, 2013, U.S. application Ser. No. 13/650,016, filed on Oct. 11, 2012, U.S. 9,681,824 (Colvin and Jiang), and U.S. Pat. No. 9,427,181 (Emken et al.), all of which are incorporated by reference in their entireties. Similarly, the structure and/or function of the sensor 100 and/or transceiver 101 may be as described in one or more of U.S. application Ser. Nos. 13/761,839, 13/937,871, and 13/650,016.

In some embodiments, the sensor 100 may include a transceiver interface device, and the transceiver 101 may include a sensor interface device. In some embodiments where the sensor 100 and transceiver 101 include an antenna or antennas (e.g., inductive elements 103 and 114), the transceiver interface device may include the inductive element 114 of the sensor 100, and the sensor interface device may include the inductive element 103 of the transceiver 101. In some of the transcutaneous embodiments where there exists a wired connection between the sensor 100 and the transceiver 101, the transceiver interface device and sensor interface device may include the wired connection.

Figure 2:
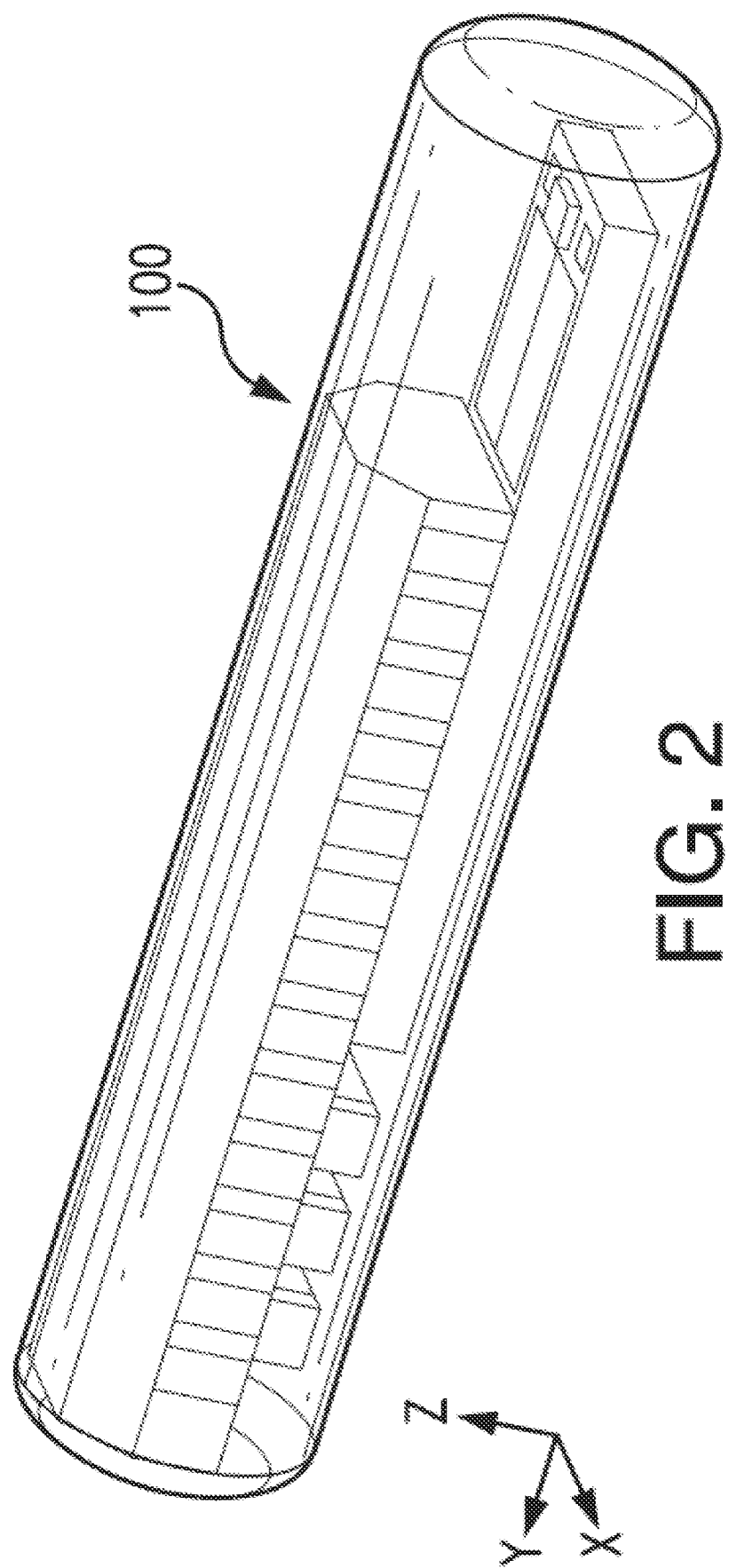
FIG. 2 illustrates a perspective view of a sensor embodying aspects of the present invention.
Figure 3:
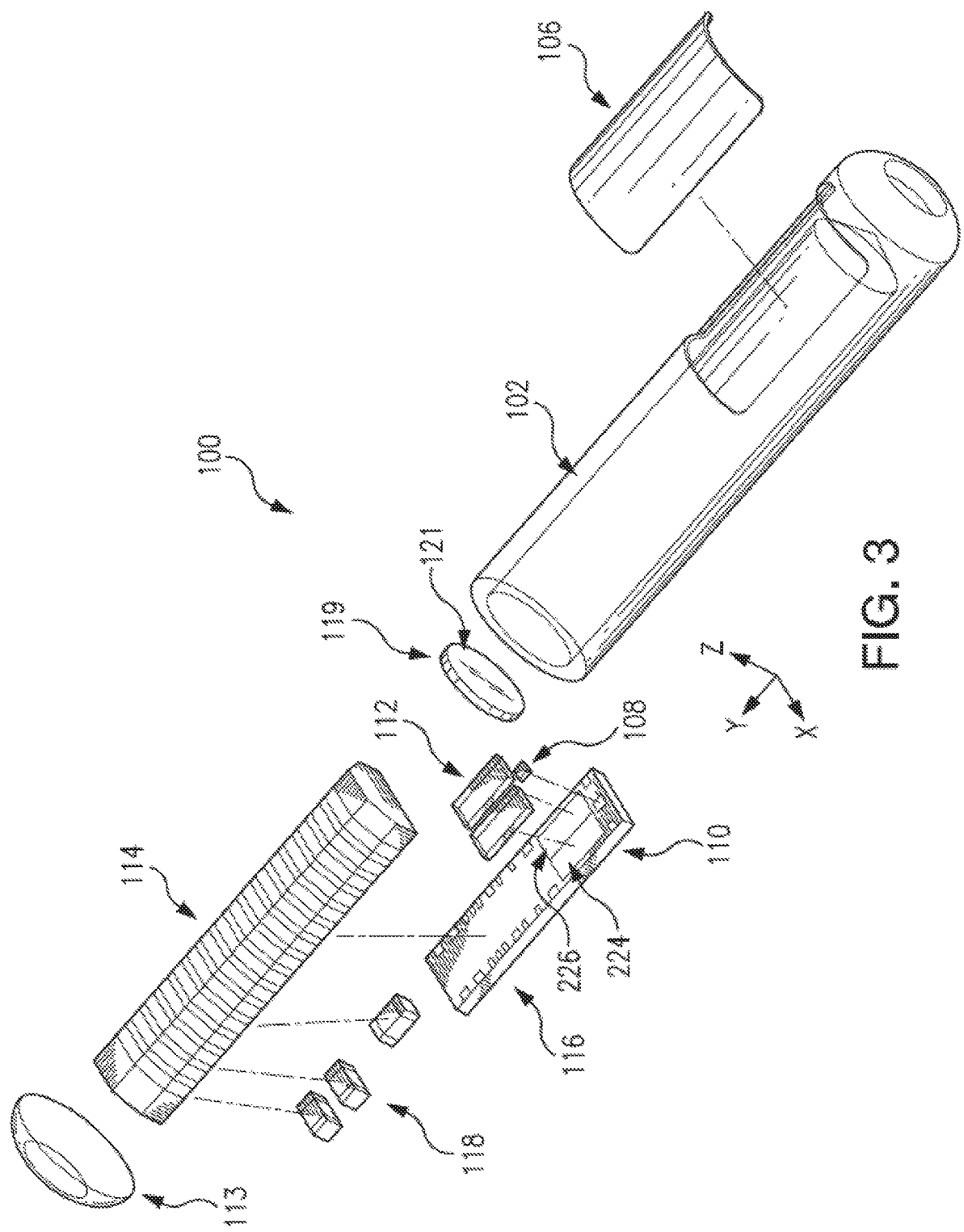
FIG. 3 illustrates an exploded view of a sensor embodying aspects of the present invention.

FIGS. 2 and 3 illustrate a non-limiting embodiment of a sensor 100 embodying aspects of the present invention that may be used in the sensor system illustrated in FIG. 1. FIGS. 2 and 3 illustrate perspective and exploded views, respectively, of the non-limiting embodiment of the sensor 100.

In some embodiments, as illustrated in FIG. 3, the sensor housing 102 may include an end cap 113. In some embodiments, the sensor 100 may include one or more capacitors 118. The one or more capacitors 118 may be, for example, one or more tuning capacitors and/or one or more regulation capacitors. The one or more capacitors 118 may be too large for fabrication in the semiconductor substrate 116 to be practical. Further, the one or more capacitors 118 may be in addition to one or more capacitors fabricated in the semiconductor substrate 116.

In some embodiments, as illustrated in FIG. 3, the sensor 100 may include a reflector 119 (i.e., mirror). Reflector 119 may be attached to the semiconductor substrate 116 at an end thereof. In a non-limiting embodiment, reflector 119 may be attached to the semiconductor substrate 116 so that a face portion 121 of reflector 119 is generally perpendicular to a top side of the semiconductor substrate 116 (i.e., the side of semiconductor substrate 116 on or in which the light source 108 and one or more photodetectors 110 are mounted or fabricated) and faces the light source 108. The face 121 of the reflector 119 may reflect radiation emitted by light source 108. In other words, the reflector 119 may block radiation emitted by light source 108 from exiting the axial end of the sensor 100.

According to one aspect of the invention, an application for which the sensor 100 was developed (although by no means the only application for which it is suitable) is measuring various biological analytes in the living body of an animal (including a human). For example, sensor 100 may be used to measure glucose, oxygen, toxins, pharmaceuticals or other drugs, hormones, and other metabolic analytes in, for example, the human body.

In some embodiments, the specific composition of the analyte indicator 106 and the indicator molecules 104 may vary depending on the particular analyte the sensor is to be used to detect and/or where the sensor is to be used to detect the analyte (e.g., in the in subcutaneous tissues, blood, or peritoneum). In some embodiments, the analyte indicator 106 facilitates exposure of the indicator molecules 104 to the analyte. In some embodiments, the indicator molecules 104 may exhibit a characteristic (e.g., emit an amount of fluorescence light) that is a function of the concentration of the specific analyte to which the indicator molecules 104 are exposed.

In some embodiments, the sensor 100 may include at least one drug eluting polymer matrix and/or a layer of catalyst and/or one or more therapeutic agents that may be provided on, incorporated in, or dispersed within the analyte indicator or sensor housing as described in U.S. Pat. No. 9,931,068 (Huffstetler et al.), which is incorporated herein by reference in its entirety. In some embodiments, the one or more therapeutic agents may be incorporated in the analyte indicator 106. In some embodiments, the sensor 100 may include a membrane covering at least a portion of the analyte indicator 106, and the one or more therapeutic agents may be incorporated within the membrane. In some embodiments, the one or more therapeutic agents include dexamethasone, triamcinolone, betamethasone, methylprednisolone, beclometasone, fludrocortisone, derivatives thereof, and analogs thereof, a glucocorticoid, an anti-inflammatory drug, e.g., a non-steroidal anti-inflammatory drug including but not limited to acetylsalicylic acid, isobutylphenylpropanoic acid.

The implantation or insertion of a medical device, such as a bio-sensor, into a user/patient's body can cause the body to exhibit adverse physiological reactions that are detrimental to the functioning of the device. The reactions may range from infections due to implantation surgery to the immunological response of a foreign object implanted in the body. That is, the performance of the implantable bio-sensor can be hindered or permanently damaged in vivo via the immunological response to an infection or the device itself. In particular, the performance of the analyte indicator 106 may be deteriorated by the immunological response of the body into which the sensor 100 is implanted. For example, as explained above, white blood cells, including neutrophils, may attack an implanted sensor 100. The neutrophils release, inter alia, hydrogen peroxide, which may degrade indicator molecules 104 (e.g., by oxidizing a boronate group of an indicator molecule 104 and disabling the ability of the indicator molecule 104 to bind glucose).

In some embodiments, the analyte indicator 106 may include one or more additives that interact or react with one or more degradative species without compromising signal integrity or performance of the sensor device. The degradative species may include one or more of hydrogen peroxide, a reactive oxygen species, a reactive nitrogen species, a free radical, an enzyme, and a metal ion. In some embodiments, the additive may be incorporated into the analyte indicator 106 that may cover at least a portion of the sensor housing 102. In some embodiments, the additive may be copolymerized with the indicator molecules 104. In some embodiments, the one or more additives may be provided in the analyte indicator 106 (e.g., polymer graft). In some embodiments, the one or more additives may interact and/or react with degradative species. In some embodiments, the one or more additives may neutralize the degradative species. In some embodiments, the one or more additives may bind to the degradative species. In some embodiments, the one or more additives may sequester the degradative species so as to inhibit, reduce, and/or prevent degradation of the analyte indicator by the degradative species. Accordingly, in some embodiments, the one or more additives reduce deterioration of the analyte indicator 106.

In some non-limiting embodiments, the one or more additives may be dithio-, thio-, or mercapto-containing moieties that interact with degradative species without compromising signal integrity or performance of the sensor.

In some non-limiting embodiments, a sensor 100 for measurement of an analyte (e.g., glucose) in a medium (e.g., interstitial fluid) within a living animal (e.g., a human) contains one or more of the following components: a sensor housing 102; a light source 108 within the sensor housing 102 configured to emit excitation light 329; an analyte indicator 106 covering a portion of the sensor housing 102; one or more indicator molecules 104 that are part of (e.g. distributed throughout) the analyte indicator 106, reversibly bind the analyte, are positioned to be irradiated by the excitation light 329, and are configured to emit light 331 indicative of the amount of the analyte in the medium within the living animal; one or more photodetectors 224 within the sensor housing 102 that are sensitive to light 331 emitted by the one or more indicator molecules 104 and configured to generate a signal indicative of the amount of the analyte in the medium within the living animal; one or more photodetectors 226 within the sensor housing 102 that are sensitive to reflection light 333 and configured to generate a reference signal indicative of the amount of received reflection light 333; and one or more compounds having dithio-, thio- or mercapto-containing moieties that interact with degradative species without compromising signal integrity or performance of the sensor 100. In some non-limiting embodiments, the sensor 100 may include a drug eluting matrix and/or a layer of catalyst provided on or incorporated in the analyte indicator 106.

In some non-limiting embodiments, one or more of the compounds having dithio-, thio- or mercapto-containing moieties may be:
    a dithio compound of Formula I: R1-S—S—R2,
    a thio compound of Formula II: R1-S—R2,
    a mercapto compound of formula III: R3-SH,
    wherein R1, R2, and R3 are each independently selected from an alkyl, an aryl, a substituted alkyl, a substituted phenyl, a substituted aryl, or a combination thereof. In some aspects, the substitute alkyl, substituted phenyl, or substituted aryl may be substituted with any appropriate molecule including, e.g., one or more halogens or halogen-containing molecules, one or more hydroxyl groups, one or more acyl groups, one or more acyloxy groups, one or more alkoxy groups, one or more aryl groups, one or more carboxy groups, one or more carbonyl groups, one or more alkylcarboxy groups, one or more alkylsufonoxy groups, one or more alkylcarbonyl groups, one or more nitro groups, one or more cyano groups, one or more acylamido groups, one or more phenyl groups, one or more tolyl groups, one or more chlorophenyl groups, one or more alkoxyphenyl groups, one or more halophenyl groups, one or more benzoxazole groups, one or more thiazoline groups, one or more benzimidazole groups, one or more oxazole groups, one or more thiazole groups, one or more indole groups, etc., or a combination thereof. In some aspects, the alkyl or substituted alkyl may be a C1 to C30 alkyl. In some aspects, the alkyl may be branched or unbranched. In some aspects, the aryl may be heterocyclic, polycyclic, or monocyclic.

In some aspects, one or more compounds having dithio-, thio- or mercapto-containing moieties may be selected from:

3,3'-Dithiodipropionic acid; 3,3'-Dithiodipropionic acid di(N-hydroxysuccinimide ester); 4,4'-Dithiodibutyric acid; Dithiodiglycolic acid; 2-Hydroxyethyl disulfide; S,S'-Methylenebis (3-Mercaptopropionic acid); Dimethyl 3,3'-dithiopropionimidate dihydrochloride; 3-Mercaptopropionic acid; 6,6'-Dithiodinicotinic acid; Dimethyl 3,3'-dithiopropionimidate dihydrochloride; Lipoic acid; 1,2-Dithiolane-3-pentanoic acid; Lipoic acid, reduced; Thioctic acid; ditridecyl thiodipropionate; distearyl thiodipropionate; dimyristyl thiodipropionate; Dilauryl thiodipropionate; 3,3'-Thiodipropionic acid; 3,3'-Thiodipropionic acid; Didodecyl 3,3'-thiodipropionate; 2,2'-Thiodiacetic acid; 4,4'-Thiodiphenol; Thiodipropionic acid dilauryl ester; 3,3'-Thiodipropanol; Glutathione; 2,2'-(Ethylenedithio)diacetic acid; Ergothioneine; Methionine; 3-Mercaptopropane-1,2-dio; dithionate salts including but not limited to sodium salts thereof; thioglycolate salts including but not limited to sodium salts thereof; thiomalate salts including but not limited to sodium salts thereof; and Lipoyllysine.

In some aspects, one or more compounds having dithio-, thio- or mercapto-containing moieties may be selected from cysteine and derivatives thereof including but not limited to N-Acetyl Cysteine, cysteic acid, homocysteic acid, cysteine sulfinic acid, and compounds represented by Formula IV:

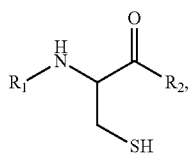

[Formula IV]

1: $R_1$ = Bz, $R_2$ = $OCH_3$
2: $R_1$ = Bz, $R_2$ = OH
3: $R_1$ = Bz, $R_2$ = $O^-$
4: $R_1$ = Ac, $R_2$ = $OCH_3$
5: $R_1$ = Ac, $R_2$ = OH
6: $R_1$ = Ac, $R_2$ = $O^-$
7: $R_1$ = H,
  $R_2$ = $OCH_2CH_3$

[Formula IV], or a salt, ester, hydrate, solvate, or amide thereof. Examples of suitable base salts, hydrates, esters, or solvates include hydroxides, carbonates, and bicarbonates of ammonia, alkali metal salts such as sodium, lithium and potassium salts, alkaline earth metal salts such as calcium and magnesium salts, aluminum salts, and zinc salts. Organic bases suitable for the formation of pharmaceutically acceptable base addition salts, hydrates, esters, or solvates of the compounds of the present invention include those that are non-toxic and strong enough to form such salts, hydrates, esters, or solvates. For purposes of illustration, the class of such organic bases may include mono-, di-, and trialkylamines, such as methylamine, dimethylamine, triethylamine and dicyclohexylamine; mono-, di- or trihydroxyalkylamines, such as mono-, di-, and triethanolamine; amino acids, such as arginine and lysine; guanidine; N-methyl-glucosamine; N-methyl-glucamine; L-glutamine; N-methyl-piperazine; morpholine; ethylenediamine; N-benzyl-phenethylamine; (trihydroxy-methyl)aminoethane; and the like. See, for example, "Pharmaceutical Salts," *J. Pharm. Sci.,* 66:1, 1-19 (1977). Accordingly, basic nitrogen-containing groups can be quaternized with agents including: lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

The salts, hydrates, esters, or solvates of the basic compounds may be prepared either by dissolving the free base of a oxathiazin-like compound in an aqueous or an, aqueous alcohol solution or other suitable solvent containing the appropriate acid or base, and isolating the salt by evaporating the solution. Alternatively, the free base of the oxathiazin-like compound may be reacted with an acid, as well as reacting the oxathiazin-like compound having an acid group thereon with a base, such that the reactions are in an organic solvent, in which case the salt separates directly or can be obtained by concentrating the solution.

In some non-limiting embodiments, the one or more compounds having dithio-, thio- or mercapto-containing moieties may be provided in the analyte indicator 106 (e.g., polymer graft or hydrogel) of the analyte sensor 100. In some non-limiting aspects, the one or more compounds having dithio-, thio- or mercapto-containing moieties are entrapped in a hydrogel covering at least a portion of the sensor housing, and the hydrogel entrapping the one or more compounds having dithio-, thio- or mercapto-containing moieties is separate and distinct from the analyte indicator. In some non-limiting embodiments, one or more compounds having dithio-, thio- or mercapto-containing moieties may be incorporated into the analyte indicator 106 by a method including one or more of the followings steps: (i) providing the analyte indicator 106 on the outer surface of the sensor housing 102, (ii) preparing a composition including the one or more compounds having dithio-, thio- or mercapto-containing moieties (e.g., preparing a solution of the one or more compounds having dithio-, thio- or mercapto-containing moieties in a solvent), (iii) inserting the analyte sensor 100 into the composition for an amount of time sufficient to effect soaking of the composition into the analyte indicator 106 on the sensor housing 102, (iv) removing the analyte sensor 100 from the composition, and (v) drying the analyte sensor 100. In some aspects, the solvent may include, for example and without limitation, an alcohol (e.g., isopropanol, ethanol, or methanol), water, or a combination thereof. In some aspects, the composition may include, for example and without limitation, about 0.01 to about 25% by weight of the compounds having one or more compounds having dithio-, thio- or mercapto-containing moieties (e.g., 0.01, 0.05, 0.1, 0.5, 1, 2, 5, 10, 15, 20, 25% by weight, or any integer or fraction thereof falling in the range between 0.01 and 25% by weight of the composition of the compounds having one or more compounds having dithio-, thio- or mercapto-containing moieties). In some aspects, the analyte sensor 100 may remain in the composition for amount of time in a range from about 5 minutes to about 24 hours (e.g., 5, 10, 20, 30, 40, 50, or 60 minutes, or 2, 4, 6, 8, 10, 12, 14, 16, 18, 20, 22, or 24 hours, or any specific time period falling in the range between 5 minutes and 24 hours). In some aspects, the analyte sensor 100 may be air dried.

In some aspects, the one or more compounds having dithio-, thio- or mercapto-containing moieties may be polymerized as a co-monomer with an indicator monomer and one or more acrylate monomers. In some non-limiting embodiments, one or more compounds having dithio-, thio- or mercapto-containing moieties may be provided as co-monomers of four monomers according to Formula V:

ABCD                                    [Formula V], wherein A is an indicator monomer, B is a methacrylate monomer, C is a polyethylene glycol monomer, and D is a dithio-, thio- or mercapto-containing moiety monomer, wherein A is 0 to 10% by weight, B is 1 to 99% by weight, C is 1 to 99% by weight, and D is 1 to 99% by weight of the total polymer.

In some non-limiting embodiments, the analyte indicator 106 may contain: (i) the TFM fluorescent indicator, (ii) hydroxyethylmethacrylate (HEMA), which is a methacrylate, (iii) polyethylene glycol (PEG), and (iv) one or more compounds having dithio-, thio- or mercapto-containing moieties. In some embodiments, the PEG may be polyethylene glycol methacrylate (PEG-methacrylate) or polyethylene glycol diacrylate (PEG-diacrylate or PEGDA). In some embodiments, i) through iv) may be provided in specific weight ratios. For example, in some non-limiting embodiments in which the analyte indicator 106 is opaque, the analyte indicator 106 may comprise 0.001 to 10% by weight, HEMA may comprise 1 to 99% by weight, PEGDA may comprise 1 to 99% by weight of the total polymer, and the one or more compounds having dithio-, thio- or mercapto-containing moieties may comprise 0.01 to 200% by weight of the total polymer.

In some embodiments, the relative molar percent of the one or more compounds having dithio-, thio- or mercapto-containing moieties may be within a specific range. In some embodiments, the relative mass percent of the one or more compounds having dithio-, thio- or mercapto-containing moieties ranges between 0.01 and 200 percent of the total polymer.

In some embodiments, the PEGDA may act as a cross-linker and create a sponge-like matrix/hydrogel. In some non-limiting embodiments, the PEG-containing graft/hydrogel may become clear if a sufficient amount of additional PEG is added to the mixture (i.e., if it is fabricated with a higher concentration of PEG), and a clear polymer graft 106 may be made from such a formulation. In some embodiments, the polymer graft may be synthesized using conventional free radical polymerization.

In some embodiments, an implanted sensor including an additive-containing analyte indicator may have improved performance over a sensor that does not include an additive-containing analyte indicator. For instance, in some non-limiting embodiments, the additive may improve the longevity and/or functionality of the sensor 100.

FIG. 4 shows experimental results of sensor longevity comparing sensors having no dithio-, thio- or mercapto-containing moieties (Control) with non-limiting embodiments of sensors 100 having one or more compounds having dithio-, thio- or mercapto-containing moieties in the analyte indicator 106 implanted subcutaneously in guinea pigs for up to 90 days.

Device samples were produced by first making the controls where the indicator hydrogels did not contain dithio or other additives. The investigational devices were produced by taking some of the control devices, and thereafter soaking for one hour at ambient temperature inside 5% (by weight) solutions of 3,3-dithiodipropionic acid (DTDP) in ethanol, followed by air-drying for 16 hours. Controls and investigational devices were implanted in the subcutaneous regions of guinea pigs. Necropsies were conducted after different points of time (0, 30, 48, 65, and 90 days), and the fluorescence signals of the explanted devices were measured using fluorometers. Fluorescence signals were measured at 0 mM and 18 mM glucose concentrations, and % Glucose modulations were calculated as follows: % Glucose Modulation= [1−(Signal at 18 mM glucose)/(Signal at 0 mM glucose)]× 100. % Glucose modulations at different points of times were normalized with respect to Day 0, or in other words un-implanted devices.

FIG. 4 shows that the % modulations of control as well as investigational devices diminished with increasing durations of being implanted. However, at all time-points, the investigational devices (DTDP) were consistently greater than the controls. For example, on Day=65 the Investigational device containing DTDP was modulating at 63% of its original Day 0 signal, whereas the Control was modulating at significantly lower modulation of 28%. This shows that that DTDP additives helped retain significantly greater glucose modulation power in the indicator hydrogel.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, although in some embodiments, the analyte sensor 100 may be an optical sensor, this is not required, and, in one or more alternative embodiments, the analyte sensor may be a different type of analyte sensor, such as, for example, an electrochemical sensor, a diffusion sensor, or a pressure sensor. Also, although in some embodiments, the analyte sensor 100 may be an implantable sensor, this is not required, and, in some alternative embodiments, the analyte sensor may be a transcutaneous sensor having a wired connection to an external transceiver. For example, in some alternative embodiments, the analyte sensor 100 may be located in or on a transcutaneous needle (e.g., at the tip thereof). In these embodiments, instead of wirelessly communication using an antenna (e.g., inductive element 114), the analyte sensor may communicate with the external transceiver using one or more wires connected between the external transceiver and a transceiver transcutaneous needle including the analyte sensor. For another example, in some alternative embodiments, the analyte sensor may be located in a catheter (e.g., for intravenous blood glucose monitoring) and may communicate (wirelessly or using wires) with an external transceiver.

What is claimed is:

1. A sensor for measurement of an analyte in a medium within a living animal, the sensor comprising:
   a sensor housing;
   an analyte indicator covering at least a portion of the sensor housing; and
   one or more compounds having dithio-, thio- or mercapto-containing moieties, wherein the one or more compounds having dithio-, thio-, or mercapto-containing moieties reduce a degradation rate of the analyte indicator and are selected from:
   a) 3,3'-Dithiodipropionic acid, 4,4'-Dithiodibutyric acid, Dithiodiglycolic acid, 2-Hydroxyethyl disulfide, S,S'-

Methylenebis (3-Mercaptopropionic acid), 3-Mercaptopropionic acid, 6,6'-Dithiodinicotinic acid, Lipoic acid, 1,2-Dithiolane-3-pentanoic acid, Lipoic acid, reduced, Thioctic acid, ditridecyl thiodipropionate, distearyl thiodipropionate, dimyristyl thiodipropionate, Dilauryl thiodipropionate, 3,3'-Thiodipropionic acid, 3,3'-Thiodipropionate, Didodecyl 3,3'-thiodipropionate, 2,2'-Thiodiacetic acid, 4,4'-Thiodiphenol, Thiodipropionic acid dilauryl ester, 3,3'-Thiodipropanol, Glutathione, 2,2'-(Ethylenedithio) diacetic acid, Ergothioneine, Methionine, 3-Mercaptopropane-1,2-diol, dithionate salts, thioglycolate salts, thiomalate salts, Lipoyllysine, and any combination thereof;
b) cysteine and compounds represented by Formula IV

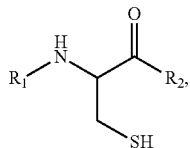

[Formula IV]

1: $R_1$ = Bz, $R_2$ = $OCH_3$
2: $R_1$ = Bz, $R_2$ = OH
3: $R_1$ = Bz, $R_2$ = $O^-$
4: $R_1$ = Ac, $R_2$ = $OCH_3$
5: $R_1$ = Ac, $R_2$ = OH
6: $R_1$ = Ac, $R_2$ = $O^-$
7: $R_1$ = H,
   $R_2$ = $OCH_2CH_3$ or a salt, ester, hydrate, solvate, or amide thereof; or
c) both a) and b).

2. The sensor of claim 1, wherein the sensor is implantable within a living animal.

3. The sensor of claim 1, wherein the one or more compounds having dithio-, thio- or mercapto-containing moieties are incorporated into the analyte indicator.

4. The sensor of claim 1, wherein the analyte indicator is a hydrogel.

5. The sensor of claim 1, wherein one or more compounds having dithio-, thio- or mercapto-containing moieties are entrapped in a hydrogel covering at least a portion of the sensor housing, and the hydrogel entrapping the one or more compounds having dithio-, thio- or mercapto-containing moieties is separate and distinct from the analyte indicator.

6. The sensor of claim 1, wherein the one or more compounds having dithio-, thio- or mercapto-containing moieties interact or react with a degradative species without compromising signal integrity or performance of the sensor device, wherein the degradative species is hydrogen peroxide, a reactive oxygen species, a reactive nitrogen species, a free radical, an enzyme, or a metal ion.

7. The sensor of claim 6, wherein the one or more compounds having dithio-, thio- or mercapto-containing moieties bind to the degradative species.

8. The sensor of claim 6, wherein the one or more compounds having dithio-, thio- or mercapto-containing moieties sequester the degradative species so as to reduce, and/or prevent degradation of the analyte indicator by the degradative species.

9. The sensor of claim 1, wherein the one or more compounds having dithio-, thio- or mercapto-containing moieties are selected from:

cysteine and compounds represented by Formula IV:

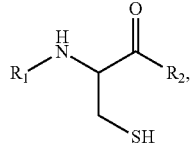

[Formula IV]

1: $R_1$ = Bz, $R_2$ = $OCH_3$
2: $R_1$ = Bz, $R_2$ = OH
3: $R_1$ = Bz, $R_2$ = $O^-$
4: $R_1$ = Ac, $R_2$ = $OCH_3$
5: $R_1$ = Ac, $R_2$ = OH
6: $R_1$ = Ac, $R_2$ = $O^-$
7: $R_1$ = H,
   $R_2$ = $OCH_2CH_3$ or a salt, ester, hydrate, solvate, or amide thereof.

10. The sensor of claim 1, wherein the one or more compounds having dithio-, thio- or mercapto-containing moieties are selected from N-Acetyl Cysteine, cysteic acid, homocysteic acid, cysteine sulfinic acid, or a salt, ester, hydrate, solvate, or amide thereof.

11. The sensor of claim 1, wherein the sensor comprises at least one drug eluting polymer matrix that covers at least a portion of the sensor housing.

12. The sensor of claim 1, wherein the one or more compounds having dithio-, thio- or mercapto-containing moieties are selected from:
3,3'-Dithiodipropionic acid; 4,4'-Dithiodibutyric acid; Dithiodiglycolic acid; 2-Hydroxyethyl disulfide; S,S'-Methylenebis (3-Mercaptopropionic acid); 3-Mercaptopropionic acid; 6,6'-Dithiodinicotinic acid; Lipoic acid; 1,2-Dithiolane-3-pentanoic acid; Lipoic acid, reduced; Thioctic acid; ditridecyl thiodipropionate; distearyl thiodipropionate; dimyristyl thiodipropionate; Dilauryl thiodipropionate; 3,3'-Thiodipropionic acid; 3,3'-Thiodipropionic acid, polymer-bound; Didodecyl 3,3'-thiodipropionate; 2,2'-Thiodiacetic acid; 4,4'-Thiodiphenol; Thiodipropionic acid dilauryl ester; 3,3'-Thiodipropanol; Glutathione; 2,2'-(Ethylenedithio) diacetic acid; Ergothioneine; Methionine; 3-Mercaptopropane-1,2-dio; dithionate salts; thioglycolate salts; thiomalate salts; and Lipoyllysine.

13. A method of fabricating a sensor for measurement of an analyte in a medium within a living animal, the method comprising:
inserting the sensor into a composition for an amount of time sufficient to effect soaking of the composition into the analyte indicator, wherein the sensor includes a sensor housing and an analyte indicator that covers at least a portion of the sensor housing, and the composition comprises one or more compounds having dithio-, thio- or mercapto-containing moieties; and
removing the sensor from the composition,
wherein the one or more compounds having dithio-, thio- or mercapto-containing moieties reduce a degradation rate of the analyte indicator and are selected from:
a) 3,3'-Dithiodipropionic acid, 4,4'-Dithiodibutyric acid, Dithiodiglycolic acid, 2-Hydroxyethyl disulfide, S,S'-Methylenebis (3-Mercaptopropionic acid), 3-Mercaptopropionic acid, 6,6'-Dithiodinicotinic acid, Lipoic acid, 1,2-Dithiolane-3-pentanoic acid, Lipoic acid, reduced, Thioctic acid, ditridecyl thiodipropionate, distearyl thiodipropionate, dimyristyl thiodipropionate, Dilauryl thiodipropionate, 3,3'-Thiodipropionic acid, 3,3'-Thiodipropionic acid, Didodecyl 3,3'-thiodipropionate, 2,2'-Thiodiacetic acid, 4,4'-Thiodiphenol, Thiodipropionic acid dilauryl ester, 3,3'-Thiodipropanol, Glutathione, 2,2'-(Ethylenedithio) diacetic acid, Ergothioneine, Methionine, 3-Mercaptopropane-1,2-dio, dithionate salts, thioglycolate salts, thiomalate salts, Lipoyllysine, and any combination thereof;

b) cysteine and compounds represented by Formula IV

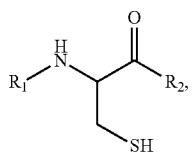

[Formula IV]

1: $R_1$ = Bz, $R_2$ = $OCH_3$
2: $R_1$ = Bz, $R_2$ = OH
3: $R_1$ = Bz, $R_2$ = $O^-$
4: $R_1$ = Ac, $R_2$ = $OCH_3$
5: $R_1$ = Ac, $R_2$ = OH
6: $R_1$ = Ac, $R_2$ = $O^-$
7: $R_1$ = H, $R_2$ = $OCH_2CH_3$ or a salt, ester, hydrate, solvate, or amide thereof; or
c) both a) and b).

14. The method of claim 13, further comprising applying an analyte indicator to a sensor housing of the sensor such that the applied analyte indicator covers at least a portion of the sensor housing before the inserting step.

15. The method of claim 13, further comprising preparing the composition comprising the one or more compounds having dithio-, thio- or mercapto-containing moieties before the inserting step.

16. The method of claim 13, wherein the amount of time is sufficient to effect soaking of the composition into the analyte indicator.

17. The method of claim 13, wherein the composition comprises the one or more compounds having dithio-, thio- or mercapto-containing moieties and a solvent.

18. The method of claim 17, wherein the solvent comprises an alcohol, water, or a combination thereof.

19. The method of claim 13, wherein the composition comprises about 0.01 to about 25% by weight of the compounds having one or more compounds having dithio-, thio- or mercapto-containing moieties.

20. The method of claim 13, wherein the amount of time is between about 5 minutes and about 24 hours.

21. The method of claim 13, wherein the one or more compounds having dithio-, thio- or mercapto-containing moieties are entrapped in a hydrogel covering at least a portion of the sensor housing, and the hydrogel entrapping the one or more compounds having dithio-, thio- or mercapto-containing moieties is separate and distinct from the analyte indicator.

22. The method of claim 13, wherein the one or more compounds having dithio-, thio- or mercapto-containing moieties reduce oxidation of the analyte indicator.

23. The method of claim 13, wherein the one or more compounds having dithio-, thio- or mercapto-containing moieties interact or react with a degradative species without compromising signal integrity or performance of the sensor device, wherein the degradative species is hydrogen peroxide, a reactive oxygen species, a reactive nitrogen species, an enzyme, a free radical, or a metal ion.

24. The method of claim 23, wherein the one or more compounds having dithio-, thio- or mercapto-containing moieties sequester the degradative species so as to reduce and/or prevent degradation of the analyte indicator by the degradative species.

25. The method of claim 13, wherein the one or more compounds having dithio-, thio- or mercapto-containing moieties are selected from:

cysteine and compounds represented by Formula IV:

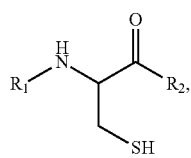

[Formula IV]

1: $R_1$ = Bz, $R_2$ = $OCH_3$
2: $R_1$ = Bz, $R_2$ = OH
3: $R_1$ = Bz, $R_2$ = $O^-$
4: $R_1$ = Ac, $R_2$ = $OCH_3$
5: $R_1$ = Ac, $R_2$ = OH
6: $R_1$ = Ac, $R_2$ = $O^-$
7: $R_1$ = H, $R_2$ = $OCH_2CH_3$ or a salt, ester, hydrate, solvate, or amide thereof.

26. The method of claim 13, wherein the one or more compounds having dithio-, thio- or mercapto-containing moieties are selected from N-Acetyl Cysteine, cysteic acid, homocysteic acid, cysteine sulfinic acid, or a salt, ester, hydrate, solvate, or amide thereof.

27. The method of claim 13, further comprising covering at least a portion of the sensor housing with at least one drug eluting polymer matrix.

28. The method of claim 13, wherein the one or more compounds having dithio-, thio-, or mercapto-containing moieties are selected from: 3,3'-Dithiodipropionic acid; 4,4'-Dithiodibutyric acid; Dithiodiglycolic acid; 2-Hydroxyethyl disulfide; $,S'-Methylenebis (3-Mercaptopropionic acid); 3-Mercaptopropionic acid; 6,6'-Dithiodinicotinic acid; Lipoic acid; 1,2-Dithiolane-3-pentanoic acid; Lipoic acid, reduced; Thioctic acid; ditridecyl thiodipropionate; distearyl thiodipropionate; dimyristyl thiodipropionate; Dilauryl thiodipropionate; 3,3'-Thiodipropionic acid; 3,3'-Thiodipropionic acid; Didodecyl 3,3'-thiodipropionate; 2,2'-Thiodiacetic acid; 4,4'-Thiodiphenol; Thiodipropionic acid dilauryl ester; 3,3'-Thiodipropanol; Glutathione; 2,2'-(Ethylenedithio) diacetic acid; Ergothioneine; Methionine; 3-Mercaptopropane-1,2-dio; dithionate salts; thioglycolate salts; thiomalate salts; and Lipoyllysine.

* * * * *